United States Patent [19]

Berkowitz

[11] 4,122,268

[45] Oct. 24, 1978

[54] TETRACHLOROAMMELIDE AND PROCESS FOR MAKING SAME

[75] Inventor: Sidney Berkowitz, Highland Park, N.J.

[73] Assignee: FMC Corporation, Philadelphia, Pa.

[21] Appl. No.: 826,440

[22] Filed: Aug. 22, 1977

Related U.S. Application Data

[63] Continuation-in-part of Ser. No. 745,146, Nov. 26, 1976, abandoned.

[51] Int. Cl.² ............................................. C07D 251/46
[52] U.S. Cl. ..................................................... 544/194
[58] Field of Search ......................................... 544/194

[56] References Cited

U.S. PATENT DOCUMENTS

| 2,184,886 | 12/1939 | Muskat et al. | 544/194 |
| 2,472,361 | 6/1949 | Arsem | 544/199 |
| 2,828,308 | 3/1958 | Lorenz | 544/194 |

Primary Examiner—John M. Ford

[57] ABSTRACT

Novel composition of matter having the formula:

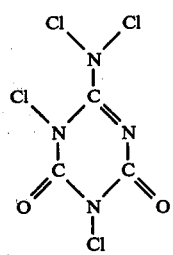

and process for making the same by chlorinating ammelide in an aqueous reaction medium.

9 Claims, 4 Drawing Figures

RAMAN SPECTRUM OF TETRACHLOROAMMELIDE

TETRACHLOROAMMELIDE
X430

TETRACHLOROAMMELIDE AND PROCESS FOR MAKING SAME

This application is a continuation-in-part of U.S. Application Ser. No. 745,146, filed Nov. 26, 1976, now abandoned.

This invention relates to a novel N-chloro heterocyclic compound, tetrachloroammelide, and to a method for preparing the same by chlorinating ammelide in an aqueous reaction medium.

N-chloro heterocyclic compounds have been prepared by numerous processes. Potashnik and Vavilina have disclosed in USSR Pat. No. 143,382 (1964) (Chemical Abstracts 62, 10452g) a process for preparing mono-, di-, and trichloro melamine by reacting melamine with hexachloromelamine at 20° to 50° C. in an aqueous medium, followed by washing the filtered precipitate with water and drying. British Pat. No. 1,092,994 (African Explosives and Chemical Industries Ltd.) discloses preparing hexachloromelamine by passing chlorine for one hour through an aqueous mixture containing melamine and sodium acetate. The resulting precipitate is washed with acetic acid, ground in the presence of carbon tetrachloride and dried at 80° C.

U.S. Pat. No. 2,828,308, issued to Lorenz on March 25, 1958, discloses purifying trichloroisocyanuric acid with sulfuric acid at temperatures below 15° C. to remove various N-chloro heterocyclic compounds such as N-chloroammelide, which has the formula:

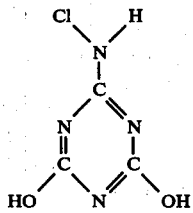

Hirsch and Slezak disclose in U.S. Pat. 3,040,044 (1962) and in the *Journal of Organic Chemistry*, Volume 25, pages 1672-3 (1960), the formation of 1,3,5-trichloro-2,4-dioxohexahydro-1,3,5-triazine having the formula:

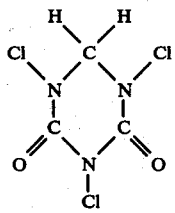

by adding chlorine with stirring at 9° to 13° C. for two hours to 2,4-dioxohexahydro-1,3,5-triazine in water while the pH is maintaned at 2.0 to 2.5 by dropwise addition of 6 N sodium hydroxide.

In U.S. Pat. No. 2,184,886, Muskat et al disclose the chlorination of heterocyclic nitrogen compounds, including ammeline, ammelide and melamine, to form mixtures of N-chloro derivatives of such imides and amides of cyanuric acid. The exact chemical structures present in these N-chlorinated product mixtures are stated to be unknown.

Arsem, in U.S. Pat. No. 2,472,361, teaches the preparation of organic N-halogen compounds such as N-halogenated derivatives of cyanuric acid amides, N-hexachlor triethylene tetramie, and other N-halogenated polyethylene polyamines. These N-halo compounds are obtained by reacting their N-hydrogen precursor compounds with a hypohalogen acid in weakly acid solutions, as in the preparation of N-hexachloro melamine by reacting a hypochlorous acid solution with melamine suspended or dissolved in water containing acetic acid to maintain the pH below 7.

The novel compound of this invention is a crystalline tetrachloroammelide having a distinct X-ray diffraction pattern and general formula:

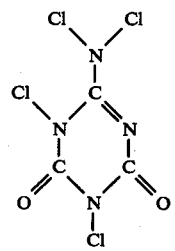

The tetrachloroammelide of this invention has an available chlorine content of 104.5% (theoretical available chlorine 106.7%). The crystals are tan colored and are well defined orthorhombic plates. Decomposition of the crystals occurs at 175° C. with heat of decomposition being −60.5K cal/mole. The high available chlorine content of the tetrachloroammelide compound of this invention renders this compound extremely useful in bleaching, sterilizing, and disinfecting operations.

The novel tetrachloroammelide compound of this invention is prepared by chlorinating ammelide in an aqueous reaction medium that is maintained at a temperature of 0° C. to 30° C. during the reaction. The aqueous reaction medium contains sodium hydroxide, which promotes dissolution of the ammelide into the alkaline reaction medium. Sufficient chlorine is added to the aqueous reaction medium to obtain a chlorine:ammelide ratio of four moles chlorine to one mole ammelide in the reaction product. Furthermore, the amount of sodium hydroxide that is present in the aqueous reaction medium is adjusted such that a pH of about 2.0 to 4.5 is obtained in the aqueous reaction medium upon completion of the ammelide chlorination. At the controlled pH of 2.0 to 4.5, the tetrachloroammelide reaction product precipitates from solution. The precipitated tetrachloroammelide may thereafter be recovered from the aqueous reaction medium.

The process of the invention permits the formation of the novel tetrachloroammelide in high yields, that is, in amounts of at least 85% and preferably at least 90% based on starting ammelide, by employing a single stage reactor. It also permits the recovery of tetrachloroammelide in exceptionally high purities in relatively short reaction times.

Figure 1:
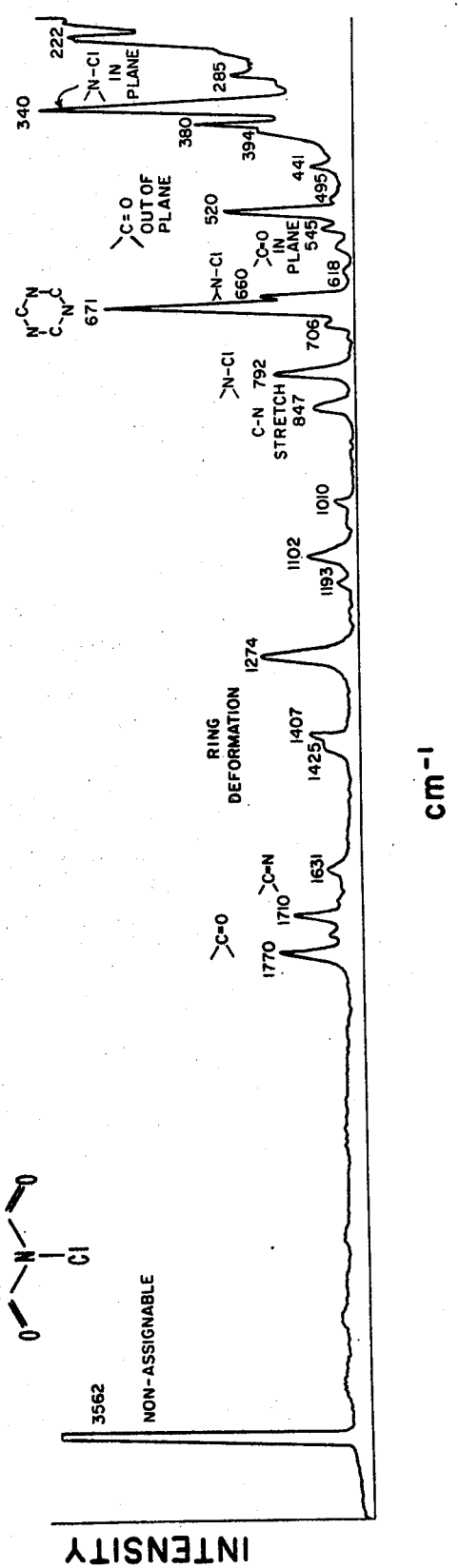
FIG. 1 represents the Raman Spectra of tetrachloroammelide crystals.

In the process of the invention, ammelide is chlorinated with a sufficient amount of chlorine to provide a molar ratio of chlorine, expressed as Cl₂ or HOCl, to ammelide of 4:1 in the reaction product. It should be noted that where gaseous chlorine is employed, a slight excess of chlorine beyond 4 moles Cl₂ per mole of ammelide may have to be added to the reaction medium to compensate for chlorine losses and reaction inefficiencies and thereby insure that 4 moles of the added chlorine are reacted with each mole of ammelide.

The 4:1 molar ratio of chlorine to ammelide provides for the complete N-chlorination of all of the available sites on the ammelide molecule that can be N-chlorinated. Any stoichiometry less than four moles chlorine to each mole ammelide results in the undesirable production of mixtures containing tetrachloroammelide and other chlorinated products. At slightly lower mole ratios, mixtures are prepared containing chlorinated ammelides, such as dichloro-, trichloro- and some tetrachloroammelide. At slightly higher mole ratios, the tetrachloroammelide begins to dechlorinate and mixtures of tetrachloroammelide and chlorinated isocyanuric acids are obtained.

Ammelide is employed in amounts of from 2 to 30% by weight based on the weight of the aqueous reaction medium. The ammelide concentration is not critical. However, from a commercial process standpoint, ammelide concentrations below 2% are not economical in view of the small amount of material being treated. Likewise, slurry concentrations above 30% are difficult to handle and accordingly are not advisable. Preferably, the ammelide concentration is between 5 and 10% by weight based on the weight of the aqueous reaction medium.

The ammelide to be reacted is contained in an aqueous reaction medium which also contains sodium hydroxide. Because of the presence of the sodium hydroxide, the aqueous reaction medium is highly alkaline, having a pH of about 14. Ammelide is not very soluble in neutral aqueous solutions, so the sodium hydroxide serves to promote dissolution of the ammelide into the alkaline reaction medium. At high ammelide concentrations, i. e., around 30% ammelide by weight, a slurry of ammelide is obtained. At low ammelide concentrations, the aqueous reaction medium is a solution containing ammelide.

The aqueous reaction medium containing ammelide may be prepared by mixing dry ammelide in an aqueous solution of sodium hydroxide. Alternatively, caustic soda (sodium hydroxide) or its solution may be dissolved in an aqueous ammelide slurry. Other methods for obtaining the aqueous reaction medium analogous to these procedures will be apparent to persons of ordinary skill in the art.

The precise amount of sodium hydroxide employed in the aqueous reaction medium depends on the amount of chlorine added to the reaction medium during the ammelide chlorination. In an aqueous medium chlorine reacts with water to form hypochloric acid and hydrochloric acid. In the alkaline reaction medium containing sodium hydroxide, the hypochlorous acid is, of course, present as sodium hypochlorite. The hypochloric acid, formed in equimolar amounts with the hypochlorous acid, is neutralized by the sodium hydroxide present in the alkaline reaction medium.

The required amount of sodium hydroxide in the aqueous reaction medium is that quantity which, when the ammelide is fully chlorinated at a ratio of 1 mole ammelide to 4 moles chlorine, is sufficient to neutralize the hydrochloric acid as well as result in the pH of the reaction medium being 2.0 to 4.5 upon completion of the ammelide chlorination. Thus, somewhat less than 1 mole of sodium hydroxide should be present initially in the aqueous reaction medium for each mole of chlorine employed in the ammelide chlorination. In actual practice, between 3.90 to 4.10 moles of sodium hydroxide per mole of ammelide being reacted are typically required.

During the ammelide chlorination reaction, the pH of the reaction medium falls from an initiall 14 to the desired 2.0 to 4.5, preferably 2.5 to 3.5, when the required 4 moles of chlorine have been completely reacted with each mole of ammelide. If excess sodium hydroxide is present initially in the aqueous reaction medium, the pH upon completion of the ammelide chlorination reaction will be higher than 4.5. If insufficient sodium hydroxide is present initially, the final pH will be highly acid, below 2.5.

Chlorine is preferably introduced into the aqueous reaction medium as a gas or liquid. Chlorination of the ammelide in the aqueous reaction medium may also be effected by introducing a hypochlorous acid solution into the reaction medium.

Addition of chlorine is continued until an amount of chlorine equivalent to four moles chlorine (Cl₂ or HOCl) per mole ammelide has been reacted with the ammelide. This amount of chlorine, as noted previously, will convert the ammelide completely to tetrachloroammelide. At this point, the pH of the reaction medium is about 2.0 to 4.5, preferably 2.5 to 3.5, when the proper amount of sodium hydroxide is present initially in the aqueous reaction medium. A pH of about 2.0 to 4.5, preferably 2.5 to 3.5 in the aqueous reaction medium upon completion of the ammelide chlorination assures optimum conversion of the ammelide into tetrachloroammelide. Higher or lower pH values should not be employed since both decrease tetrachloroammelide yields by causing product decomposition at lower pH values and salt formation at higher pH values.

Maximum conversion of the ammelide into tetrachloroammelide is achieved at temperatures from 0° to 30° C. and preferably at temperatures from 10° to 20° C. Lower temperatures tend to increase reaction time and product decomposition, whereas higher temperatures may result in the formation of mixtures containing tetrachloroammelide and chlorinated cyanuric acids by removing the tetrachloroammelide exocyclic nitrogen. Temperature control of the aqueous reaction medium is most readily obtained via external cooling means, since the chlorination reaction is exothermic.

Chlorination of the ammelide is extremely rapid under the operating conditions of this process with complete conversion being achieved in less than 30 minutes. In order to maximize product yield, the reaction is preferably carried out in less than about 20 minutes, and most preferably carried out in less than 10 minutes. These reaction times can be achieved by employing conventional reactors.

The process of this invention may be operated batchwise or continuously, employing conventional reaction process equipment and procedures.

When the reaction is carried out in the prescribed manner and the pH value of the aqueous reaction medium is maintained as specified, the tetrachloroammelide reaction product precipitates from solution. Additional tetrachloroammelide crystals may be precipitated from solution by cooling the aqueous reaction medium after completion of the ammelide chlorination.

The precipitated tetrachloroammelide may then be recovered from solution by conventional liquid-solid separatory means, such as by filtration. Optionally, the tetrachloroammelide may be treated as in intermediate and reacted further to prepare other chlorinated triazine compounds. If recovered, the tetrachloroammelide crystals are normally washed and dried in a conventional manner to remove residual moisture and to produce a free-flowing crystalline product. These procedures are well known in the art and do not constitute a part of the invention.

The invention will be better understood from a consideration of the following example. The example is given to illustrate the invention and is not deemed to be limiting thereof. All percentages given are based on weight unless otherwise indicated.

EXAMPLE

A 12.8 g (0.100 g mole) sample of ammelide (assaying 99.5% ammelide) was suspended in a solution of 16.16 g (0.404 moles) sodium hydroxide in 140 g of water. The reaction mixture was cooled by external cooling means to 14° C. and gaseous chlorine was passed into the reactor until the pH value of the reaction mixture fell from 14.0 to 2.9. The crystallized precipitate was filtered from the slurry, washed and air dried at 100° C. to remove surface moisture. The total yield was 24.3 g which is equivalent to 91.4% recovery of product as tetrachloroammelide based on starting ammelide.

The Raman spectrum of the recovered crystals, presented in FIG. 1, was obtained with a Spectra-Physics Argon Ion Laser operating at 5145A and a Spex Raman Monochrometer with photon counting light detection. The Raman effect is based on light scattered from a vibrating molecule. When light strikes the molecule, the molecule superimposes its vibrational energy upon the energy of the incoming light. Thus, the scattered light contains in addition to the main laser frequency, other frequencies corresponding to individual molecular vibrations. The Raman spectrum shown in FIG. 1 confirms that the recovered crystals were tetrachloroammelide.

Figure 2:
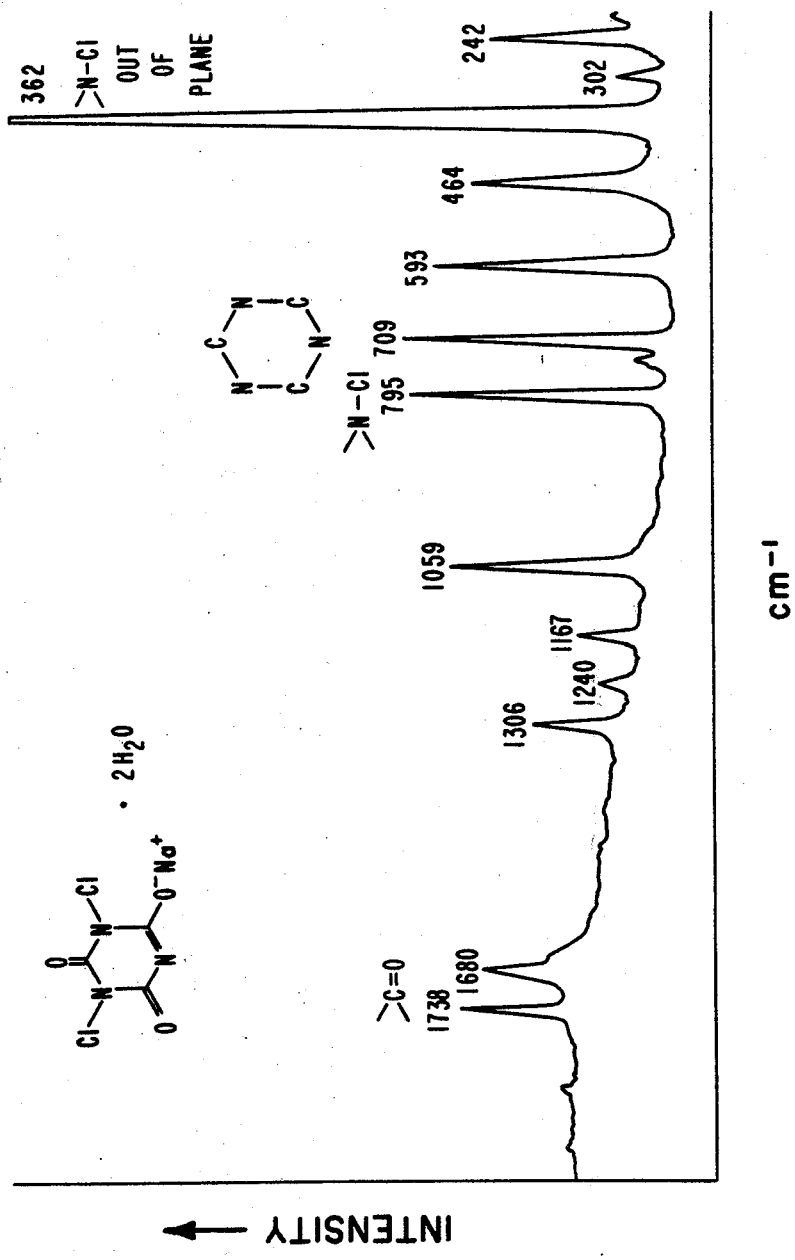
FIG. 2 represents a comparative Raman Spectra of sodium dichloroisocyanurate dihydrate.
Figure 3:
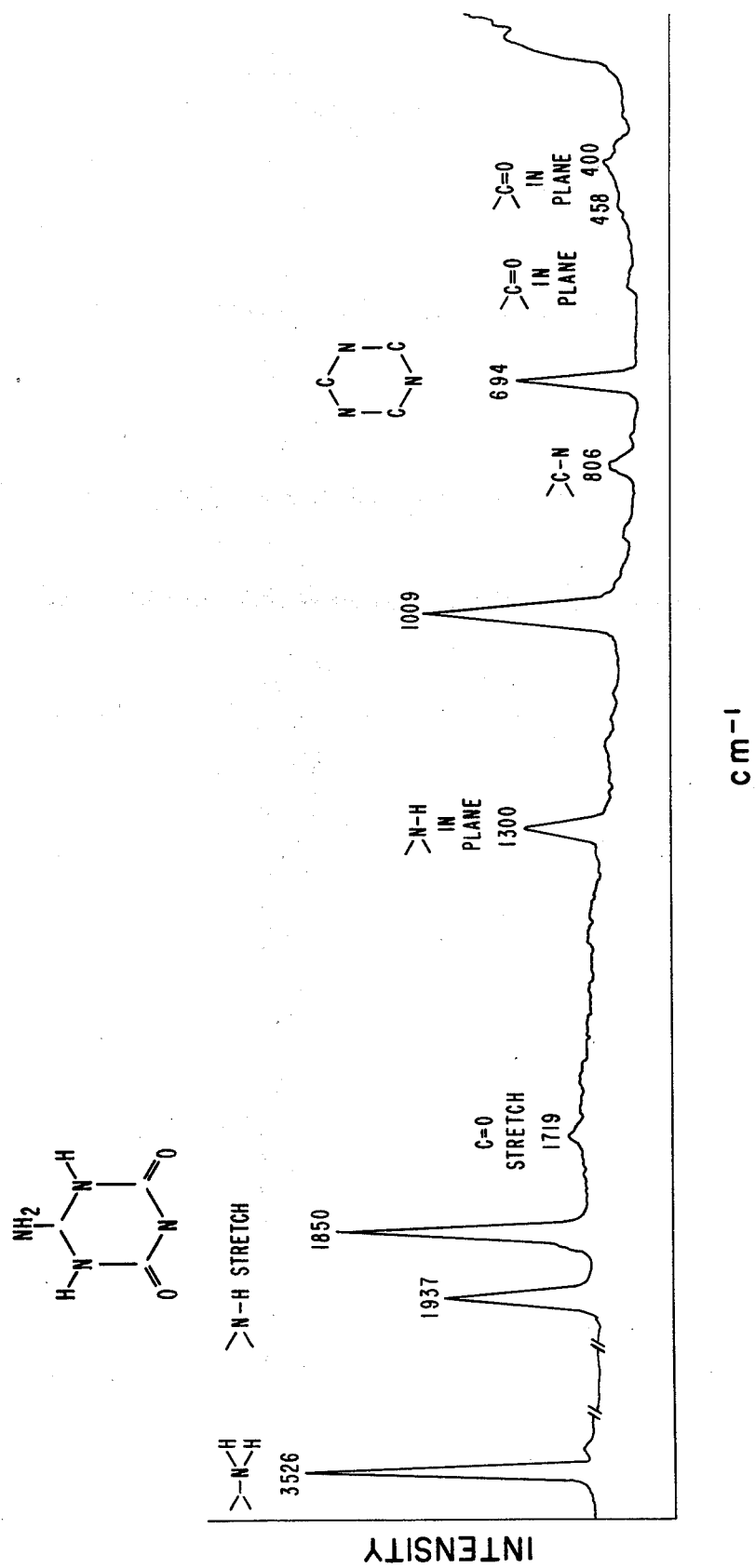
FIG. 3 represents a comparative Raman Spectra of ammelide.

Comparative Raman spectra for sodium dichloroisocyanurate dihydrate and ammelide are given in FIGS. 2 and 3 respectively.

Figure 4:
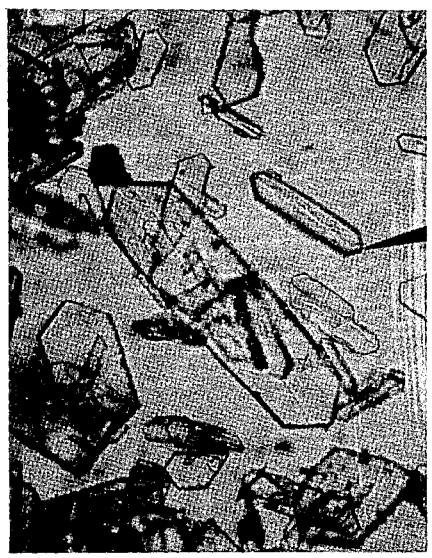
FIG. 4 is a photomicrograph of tetrachloroammelide crystals taken at 450X magnification.

FIG. 4 is a photomicrograph of the recovered tetrachloroammelide crystals taken at 450X.

The invention being thus described, it will be obvious that the same may be varied in many ways. Such variations are not to be regarded as a departure from the spirit and scope of the invention, and all such modifications are intended to be included within the scope of the following claims.

I claim:
1. Tetrachloroammelide of the formula:

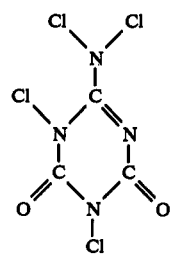

2. A process for preparing tetrachloroammelide of the formula:

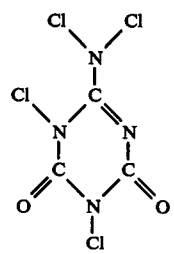

which comprises chlorinating the ammelide in an aqueous reaction medium with chlorine to form tetrachloroammelide, the reaction medium being maintained at a temperature of 0° C. to 30° C.;
 (a) wherein the aqueous reaction medium contains sodium hydroxide to promote dissolution of the ammelide;
 (b) wherein sufficient chlorine is added in the reaction medium to obtain a chlorine:ammelide ratio of about four moles chlorine to one mole ammelide in the reaction product; and
 (c) wherein the amount of sodium hydroxide present in the reaction mixture is such so as to provide a pH of about 2.0 to 4.5 in the reaction medium upon completion of the ammelide chlorination, thereby causing the tetrachloroammelide to precipitate from solution.

3. The process of claim 2 wherein the aqueous reaction medium to be chlorinated contains 2% to 30% by weight ammelide.

4. The process of claim 2 wherein the aqueous reaction medium to be chlorinated contains 5% to 10% by weight ammelide.

5. The process of claim 2 wherein the aqueous reaction medium is maintained at a temperature of 10° C. to 20° C.

6. The process of claim 2 wherein the aqueous reaction medium pH is about 2.5 to 3.5 upon completion of the ammelide chlorination.

7. The process of claim 2 wherein the precipitated tetrachloroammelide is recovered from the aqueous reaction medium.

8. The process of claim 2 wherein the ammelide chlorination is completed in less than thirty minutes.

9. The process of claim 2 wherein the amount of sodium hydroxide employed is about 3.90 to 4.10 mole per mole of ammelide.

* * * * *